US00PP09631P

United States Patent [19]

Gruppe et al.

[11] Patent Number: Plant 9,631

[45] Date of Patent: Aug. 20, 1996

[54] CHERRY ROOTSTOCK GI 195/2

[75] Inventors: Werner Gruppe, Linden; Hanna Schmidt, Ahrensburg, both of Germany

[73] Assignee: Inter-Plant Patent Marketing, Inc., Ontario, Canada

[21] Appl. No.: 485,405

[22] Filed: Jun. 7, 1995

[51] Int. Cl.[6] ..... A01H 5/00

[52] U.S. Cl. ..... Plt./37

[58] Field of Search ..... Plt./37

[56] References Cited

U.S. PATENT DOCUMENTS

P.P. 8,852 8/1994 Gruppe et al. ..... Plt./37

P.P. 8,954 10/1994 Gruppe et al. ..... Plt./37

*Primary Examiner*—James R. Feyrer

*Attorney, Agent, or Firm*—Flynn, Thiel, Boutell & Tanis, P.C.

[57] ABSTRACT

The new and distinct cultivar of cherry rootstock, which has been given the designation GI 195/2 produces a tree which is generally spreading and which upon grafting produces a dwarf tree.

2 Drawing Sheets

FIELD OF THE INVENTION

The present invention relates generally to cherry trees and more specifically to a new and distinct variety of cherry hybrid tree which is particularly useful as a rootstock.

BACKGROUND OF THE INVENTION

The use of cherry hybrid trees as rootstock is known in the art of producing cherry trees. One such variety is F12/1, a vegetatively propagated P. avium-selection. Rootstock varieties of GI 148/2 and GI 148/8 are described in U.S. Plant Patents 8852 and 8954 respectively. The use of cherry hybrid varieties as rootstock produces a dwarf tree that comes into earlier and heavier bearing without sacrificing fruit size.

SUMMARY OF THE INVENTION

The new and distinct cultivar of cherry rootstock, which has been given the designation GI 195/2 produces a tree which is generally spreading and which upon grafting produces a dwarf tree.

DETAILED DESCRIPTION OF THE INVENTION

Figure 1:
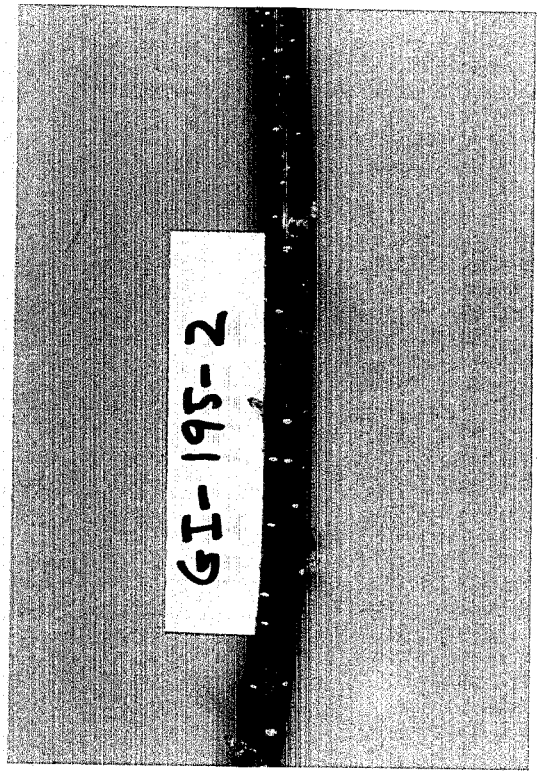
FIG. 1 illustrates a branch and dormant lateral buds, bark and lenticels of GI 195/2.
Figure 2:
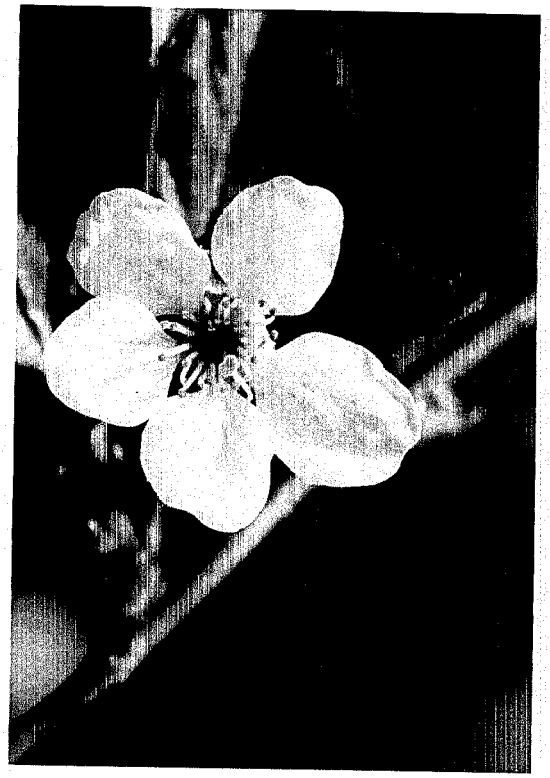
FIG. 2 illustrates GI 195/2 flowers.

The new and distinct variety of cherry hybrid tree of the present invention was bred by the inventors as a cross of *Prunus canescens*×*Prunus cerasus* cv. "Leitzkauer" with *Prunus canescens* in Giessen, Germany. It has been successfully asexually propagated by softwood cuttings at the University of Giessen in Giessen, Germany, and has been observed to remain true to the description set forth herein.

GI 195/2 as used as a rootstock for sweet cherry trees induces dwarfing to a significant degree. Precocity, high production of fruit and yield efficiency, good fruit size and no or very few suckers were induced. GI 195/2 as a rootstock confers earlier and heavier bearing to the scion as compared to F12/1 clonal cherry rootstock. As a mean of seven years, 100-fruit-weight of "Hedelfinger" grafted on 195/2 was 737 grams, while 100-fruit-weight of "Hedelfinger" grafted on F12/1 was 735 grams.

GI 195/2 itself is bushy, of medium vigor and has medium frosthardiness. After eight growing seasons near Giessen, Germany, GI 195/2 demonstrated a height of 3.30 meters and a width of 3.30 meters.

The following varieties of sweet and sour cherries have been successfully grafted onto GI 195/2: Hedelfinger, B üttners Rote Knorpel, Grosse Schwarze Knorpel, Van, and Montmorency. No graft incompatibility is presently known.

Ploidy of 195/2 is probably triploid (2n=3x). The ploidy status of the parents has been investigated by isoenzyme analysis and is tetraploid (2n=4x) for the mother plant= *Prunus cerasus,* cv "Leitzkauer", and diploid (2n=2x) for the father plant, *Prunus canescenes.*

Leaves:

*Overall shape.*—Obvate.

*Apex shape.*—Acute to slightly acuminate.

*Base shape.*—Rounded, slightly acute.

*Leaf serration.*—Doubly serrate leaf margin, secondary notches are indistinct.

*Veination.*—Pinnate, 9–11 veins, mainly alternate.

*Stipules.*—Prominent at base of petiole on most leaves.

*Glands.*—Rounded, attached to bottom edge of blade.

*Pubescence.*—Very sparse pubescence on adaxil surface (top), lightly pubescent on abaxil surface especially on veins.

*Color.*—Light green.

Leaf dimensions of GI 195/2 at 5th and 9th leaf:

| | 5th leaf | 9th leaf |
|---|---|---|
| Mean length of leaves | 59 | 80 |
| Mean width of leaves | 32 | 50 |
| Mean length of petioles | 73 | 70 |

Branches: One year old branches are very slightly pubescent, buds alternate on branch.

*Color of 2-year old branch.*—Greyed red; Fan 4, 178 B (R.H.S. Colour Chart).

Branch dimensions: (For a single GI 195/2 plant in the ungrafted condition after the 5th leaf; in brackets, comparable data for F12/1).

*Mean length of* 1-*year-old branches.*—19.0 cm (19.8 Cm).

*Mean length of* 2-*year-old branches.*—28.4 cm (35.0 cm).

*Mean length of* 3-*year-old branches.*—29.5 cm (63.2 cm).

*Mean diameter of* 1-*year-old branches.*—1.8 mm (3.4 mm).

*Mean diameter of* 2-*year-old branches.*—3.0 mm (5.8 mm).

*Mean diameter of* 3-*year-old branches.*—4.9 mm (10.1 mm).

*Mean no. of branches from* 2-*year-old branches.*—1.2 (0.7).

*Mean no. of branches from* 3-*year-old branches.*—6.4 (2.4).

*Mean no. of nodes of* 2-*year-old branches.*—12.2 (15.3).

*Mean no. of nodes of* 3-*year-old branches.*—11.4 (22.4).

*Mean angle of* 3-*year-old branches.*—75.0 (59.7).

*Mean angle of* 4-*year-old branches.*—78.3 (58.3).

Buds: Conical, acute, adpressed, 2–3 mm long, overlapping bud scales, with prominent leaf scars. No ornamental value.

Flowers:

*Flowering.*—Flowers in the 1st year.

*Abundance.*—Good flower density 2nd year.

*Petal color.*—White.

*Petal shape.*—Almost round.

Bloom:

*Begin of bloom.*—Late.

Overall vigor:

*Suckers.*—None.

Survey of growth data: Growth of one ungrafted, 60 kilometers south of Gliessen, Germany after 5th and 9th leaf is shown in Table 1 below.

TABLE 1

| | 5th leaf | 9th leaf |
|---|---|---|
| Height (cm) | 230 | 370.0 |
| Width (cm) | 185 | 380.0 |
| Depth (cm) | | 450.0 |
| Fresh weight (kg) | | 41.5 |

A crown-silhouette comparison of GI 195/2 and F12/1-(m2)=height×(width+depth)/2 is shown in Table 2.

TABLE 2

| | GI 195/2 | F12/1 |
|---|---|---|
| After 4 years in orchard: | 3.7 | 7.7 |
| After 6 years in orchard: | 5.9 | 14.3 |

Enzyme polymorphism of GI 195/2: (Studied by horizontal starch gel electrophoresis of leaf tissue of 8 loci.) is shown in Table 3.

TABLE 3

| | 195/2 |
|---|---|
| Aconitase-2 | 22 |
| Alkoholdehydrogenase-1 | 112 |
| Isocitratdehydrogenase-2 | 122 |
| Leucinaminopeptisase-1 | 23 |
| 5-Phosphogluconat-Dehydrogenase-1 | 1H |
| 6-Phosphogluconat-Dehydrogenase-2 | 122 |
| Phophoglucose-Isomerase-2 | 124 |
| Phosphoglucomutase-2 | 25 |

What is claimed is:

1. A new and distinct variety of cherry hybrid tree as shown and described herein.

* * * * *